(12) United States Patent
Gordon et al.

(10) Patent No.: US 6,773,456 B1
(45) Date of Patent: Aug. 10, 2004

(54) ADJUSTABLE CUSTOMIZED ENDOVASCULAR GRAFT

(75) Inventors: Andrew R. Gordon, Pleasanton, CA (US); Albert K. Chin, Palo Alto, CA (US); Steve G. Baker, Sunnyvale, CA (US)

(73) Assignee: Endovascular Technologies, Inc., Santa Clara, CA (US)

(*) Notice: Subject to any disclaimer, the term of this patent is extended or adjusted under 35 U.S.C. 154(b) by 17 days.

(21) Appl. No.: 09/815,477

(22) Filed: Mar. 23, 2001

(51) Int. Cl.[7] .................................................. A61F 2/06
(52) U.S. Cl. ...................................... 623/1.28; 623/1.29
(58) Field of Search ............................... 623/1.13, 1.14, 623/1.15, 1.16, 1.23, 1.27, 1.28, 1.29, 1.3, 1.31, 1.35, 1.44

(56) References Cited

U.S. PATENT DOCUMENTS

| | | | |
|---|---|---|---|
| 4,140,126 A | 2/1979 | Choudhury | |
| 5,282,847 A | 2/1994 | Trescony et al. | |
| 5,464,449 A | 11/1995 | Ryan et al. | |
| 5,476,506 A | 12/1995 | Lunn | |
| 5,522,881 A | 6/1996 | Lentz | |
| 5,593,417 A | * 1/1997 | Rhodes | 606/191 |
| 5,824,037 A | 10/1998 | Fogarty et al. | |
| 5,824,040 A | 10/1998 | Cox et al. | |
| 6,117,167 A | * 9/2000 | Goicoechea et al. | 623/1.16 |
| 6,432,131 B1 | * 8/2002 | Ravenscroft | 623/1.13 |

* cited by examiner

*Primary Examiner*—Corrine McDermott
*Assistant Examiner*—Hieu Phan
(74) *Attorney, Agent, or Firm*—Fulwider Patton Lee & Utecht, LLP (57) ABSTRACT

The present invention embodies an adjustable customized graft for placement within body lumens. The adjustable graft includes longitudinal and lateral pleats that can be individually released to thereby customize the length and lateral profile of the graft. A tubular jacket configured with access holes to the pleats is provided for delivering the adjustable graft within vasculature of the patient.

44 Claims, 5 Drawing Sheets

FIG. 14

ADJUSTABLE CUSTOMIZED ENDOVASCULAR GRAFT

BACKGROUND OF THE INVENTION

This invention relates to the treatment of body lumens and, more particularly, to the endovascular placement of a prosthetic graft within vasculature for the purpose of repairing the same.

It is well established that various fluid conducting body or corporeal lumens, such as veins and arteries, may deteriorate or suffer trauma so that repair is necessary. For example, various types of aneurysms or other deteriorative diseases may effect the ability of the lumen to conduct fluids and, in turn, may be life threatening. In some cases, the damage to the lumen is repairable only with the use of prostheses such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a graft and implanting the graft within the vasculature.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature.

Placement of a bifurcated endovascular aortic graft within vasculature is rendered difficult by the diverse variation and anatomical morphology present in different patients. In order to implant a correctly sized graft, one must consider the neck diameter, neck length, limb diameters and limb lengths of the target vasculature. For example, the left iliac diameter and length may differ substantially from the right iliac diameter and length in the same patient and the same must be considered in sizing a graft. The calculated permutations of neck and limb dimensions require to adequately treat all patients has been estimated to number approximately thirteen thousand. It is not practical, however, to manufacture and store multiple numbers of all thirteen thousand sizes of bifurcated aortic grafts, due to cost and storage considerations.

Determination of true aortic sizes is most accurately performed through an aortogram, with delineation of aortoiliac anatomy via fluoroscopic imaging of injected contrast dye. This generally occurs before or at the time of endovascular graft placement. Staging an aortogram prior to the graft placement procedure may allow a custom sized graft to be manufactured. For example, a patient may be brought in for an aortogram a significant time (e.g., one month) prior to a scheduled elective endovascular graft procedure for definitive aortoiliac sizing. A specially sized graft may be manufactured and inserted into a jacketed catheter delivery system for subsequent use.

The difficulty with this approach is twofold. First, the patient must be brought into the hospital for an additional catheter procedure, adding inconvenience and expense to the treatment regime. Second, the sizing procedure results in a delay in the treatment of the patient.

Accordingly, there exists a need for a graft that can be customized on site at the time of an implant procedure. The present invention addresses this and other needs.

SUMMARY OF THE INVENTION

Briefly and in general terms, the present invention is embodied in an adjustable customized endovascular graft. The graft of the present invention is adjustable lengthwise or longitudinally and widthwise or laterally to affect a change in diameter to provide a structure configured to adapt to irregularities in anatomy.

In one aspect of the invention, the graft is an oversized tube, tapered, unibody bifurcated, modular bifurcated, or modular tapered graft. The graft is configured with at least one or a plurality of releasable pleats along the graft body or a portion thereof. The pleats are strategically placed during manufacture to facilitate the modification of the diameter and length of various portions of the graft.

In a preferred embodiment, an outside surface of the graft of the present invention is configured with pleats across the graft. Further, the pleats are configured such that pockets formed thereby are directed away from the path of flow of blood through the interior of the graft. In this way, the graft is provided with a relatively smooth interior profile for optimal flow characteristics.

Construction of the pleats may be achieved by various methods. It is contemplated that the pleats may be formed by sewing a looped stitch in the graft wall that unravels when a free end of the stitch is pulled. A running stitch can also be used particularly in the transverse pleats that are short in length. Conventional suture material may be used for this purpose. Such stitching is employed to maintain pleated sizes and shapes when the graft is filled with pressurized blood.

A catheter embodying a jacket for receiving the adjustable graft of the present invention is contemplated to be employed for delivering the graft within vasculature. In a preferred embodiment, the jacket is configured with a plurality of holes which provide access to the pre-placed stitches forming the pleats in the adjustable graft. The tail of the suture forming the respective pleats extends through such a hole, with the suture knot residing inside the jacket. When one desires to release a given pleat, tension is applied to the corresponding suture tail to pull the knot out of the hole in the jacket and allow the pleat forming stitch to be cut and pulled out of the graft. Alternatively, a crosspiece of metal or plastic may be provided exterior each of the access holes wherethrough a portion of a stitch forming a pleat is routed and placed into engagement with the crosspiece. Each access hole is contemplated to be separately identified to thereby provide a reference respecting the location and purpose of a particular pleat. Releasing the crosspiece and pulling the suture yields desired graft dimensions.

In an alternative embodiment, the adjustable graft may include flared ends. When so configured, the adjustable graft can accommodate a greater range of diameters found in vasculature.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENTS

The present invention relates to a graft, the size of which is adjustable longitudinally and laterally. The graft of the present invention is therefore capable of being customized to fit various sized and shaped lumens. Due to this versatility, the adjustable graft of the present invention can be customized on site at the time of an implant procedure. The adjustable graft may assume a simple tubular configuration or may be bifurcated or tapered.

Figure 1:
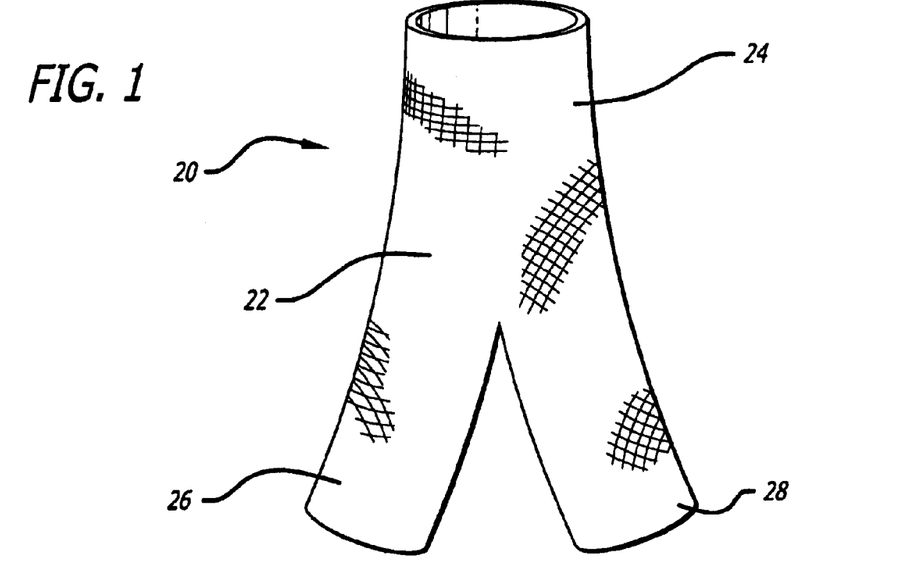
FIG. 1 is a perspective view, depicting one embodiment of a graft of the present invention.
Figure 2:
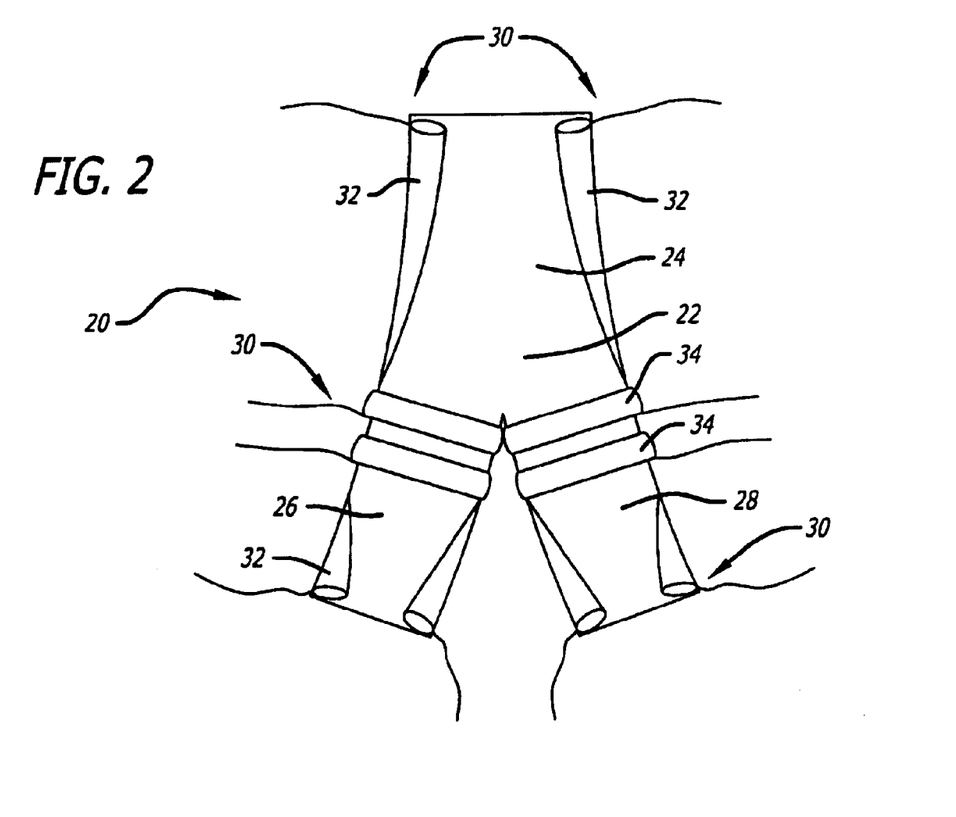
FIG. 2 is a perspective view, depicting the graft of FIG. 1 configured with a plurality of pleats.

Referring to FIGS. 1 and 2, one preferred embodiment of the adjustable graft 20 of the present invention includes a body 22 having a trunk 24 and first 26 and second 28 legs extending therefrom. The adjustable graft 20 includes a wall defining an interior path for fluid flow. When placed within vasculature, the adjustable graft 20 is configured to define a path for blood flow.

As shown in FIG. 2, the adjustable graft 20 may be adapted with one or more adjustment devices, any number of which may be manipulated to affect the size of the graft as desired. In a preferred embodiment, the adjustment devices embody sutures 30 that have been attached to the graft body 22 at strategic locations at the time of manufacture to thereby provide the graft 20 with the ability to be customized. Rivets or other connecting devices also can be used for this purpose. The sutures 30 may be configured to provide the adjustable graft 20 with both longitudinal pleats or layers 32 as well as lateral pleats or layers 34. Such connecting devices are used to maintain the pleated profile of graft during deployment within vasculature when the graft is exposed to pressurized blood. It is further contemplated that the connecting devices or sutures 30 are releasably attached to the graft body 22 in a manner such that pulling an end of the suture 30 causes the suture 30 to unravel and disengage the pleat 32, 34.

It is to be recognized that the longitudinal pleats 32 operate to affect the diameter of the graft body 22 whereas the lateral pleats 34 affect the length of the graft 20. In particular, longitudinal pleats 32 configured within the trunk 24 of the graft body 22 operate to decrease the diameter of the trunk 24. By configuring the trunk 24 with a plurality of longitudinal pleats 32, multiple alternative diameters and profiles of the trunk can be achieved. Additionally, by configuring the legs 26, 28 of a graft 20 with a plurality of longitudinal pleats 32, multiple alternative diameters and profiles of the legs likewise can be achieved.

Similarly, lateral pleats 34 configured within the trunk 24 (not shown) or legs 26, 28 (See FIG. 2) of the graft body 22, operates to affect the length of the graft 20. Moreover, adapting the graft body 22 with a plurality of lateral pleats 34 provides the graft 20 with multiple alternative length possibilities. Additionally, the same provides the graft 20 with the advantage of ultimately having legs 26, 28 of different lengths.

Although the figures depict the graft 20 having a certain number of longitudinal and lateral pleats 32, 34 placed at various positions along the graft body 22, it is to be further recognized that the graft 20 can be configured with fewer or more pleats 32, 34 at various alternative angles and positions along the body 22. Moreover, as stated, the graft 20 can assume a tubular or tapered configuration rather than a bifurcated shape.

Figure 3:
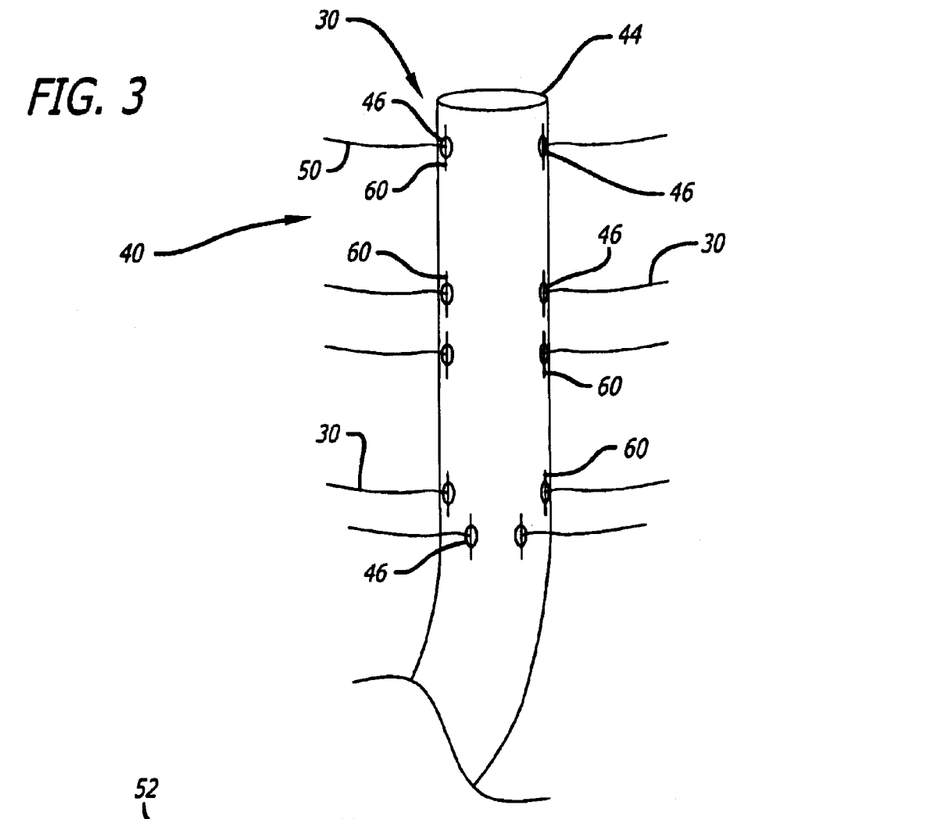
FIG. 3 is a perspective view, depicting a jacket for use with the graft of the present invention.
Figure 4:
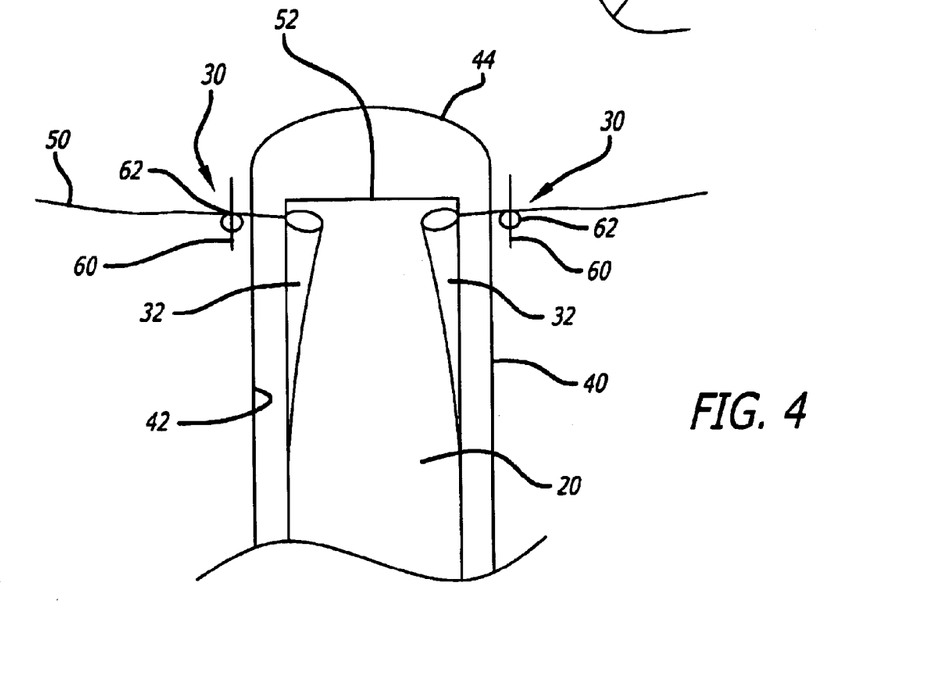
FIG. 4 is a cross-sectional view of the assembly shown in FIG. 3.

Turning now to FIGS. 3 and 4, there is shown a jacket 40 for releasably receiving the adjustable graft 20 of the present invention. The jacket 40 can embody a catheter for delivering the graft 20 to a target site or may alternatively be employed in conjunction with a delivery catheter (not shown) for accomplishing the same. Methods for accessing vasculature, for example, and intraluminally advancing delivery catheters within vasculature to a repair site are well known in the art. Such procedures typically involve employing x-ray type methods such as fluoroscopy to view the process of advancing the delivery catheter within vasculature. To aid visualization, the delivery catheter or graft can be configured with radiopaque markers. Thus, it is likewise contemplated that the jacket 40 or graft 20 itself can be configured with one or more radiopaque markers (not shown).

In a preferred embodiment, the jacket 40 has a generally tubular configuration. The jacket 40 defines an internal lumen 42 that is sized to releasably receive the graft 20 of the present invention. A superior end 44 of the jacket 40 may include an opening for egress or ingress of the graft 20. Additionally, it is contemplated that the jacket 40 further includes a plurality of holes or slits 46 in the wall defining the tubular jacket 40. These holes or slits 46 provide access to the various adjustable devices or sutures 30 attached to the graft 20.

Figure 8:
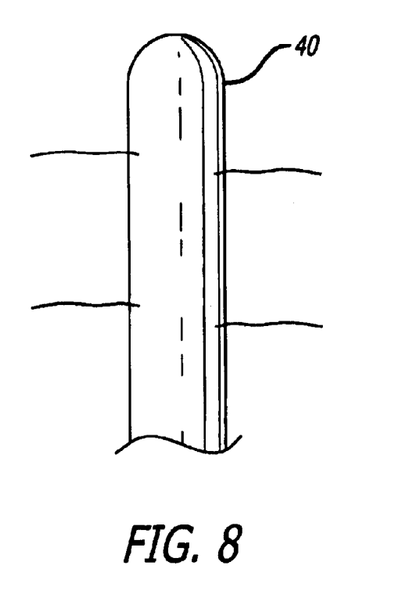
FIG. 8 is a perspective view, depicting a jacket for use with the graft of the present invention.
Figure 9:
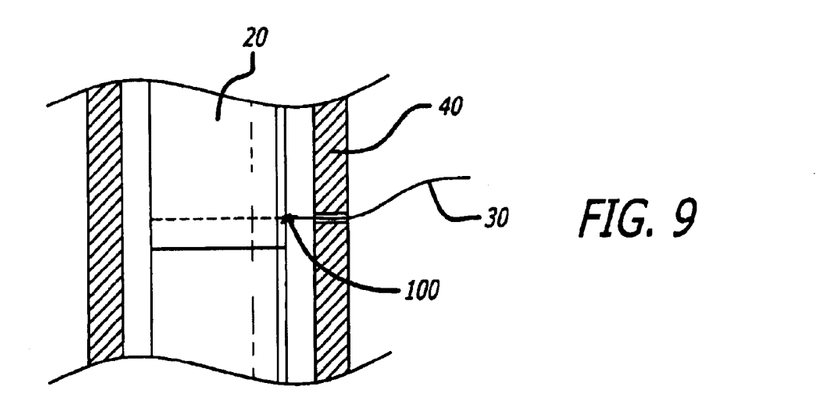
FIG. 9 is a cross-sectional enlarged view of the assembly shown in FIG. 8.
Figure 10:
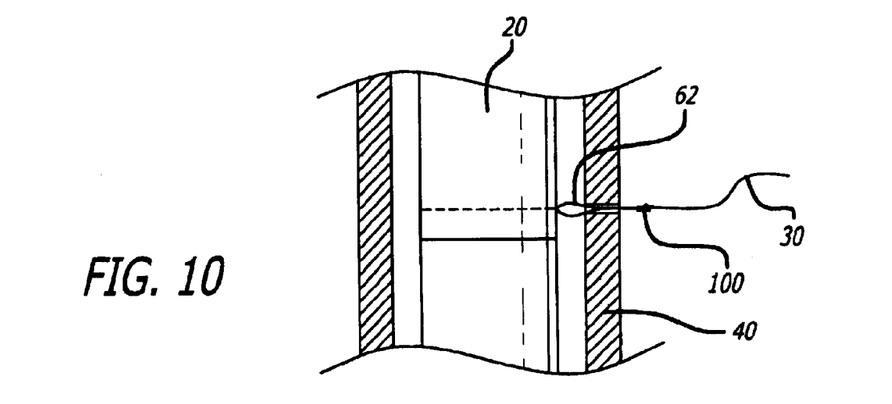
FIG. 10 is the cross-sectional enlarged view of FIG. 9, depicting the suture being pulled out of the jacket in preparation for cutting the suture that forms the pleat.
Figure 11:
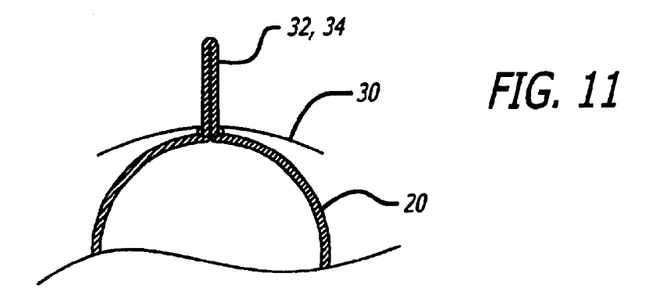
FIG. 11 is a cross-sectional view of a portion of a graft, depicting a looped suture in combination with a pleat.
Figure 12:
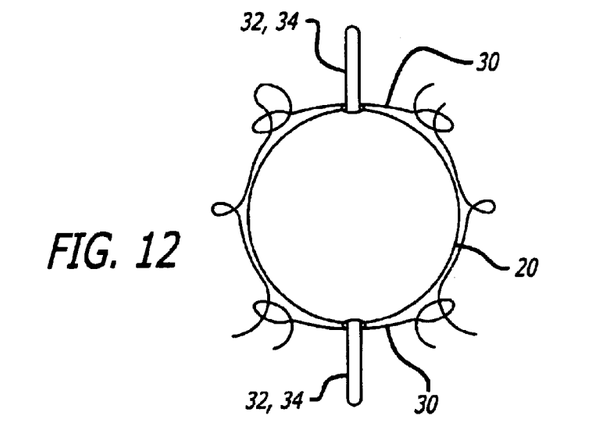
FIG. 12 is an end view, depicting a graft configured with a pair of looped sutures.
Figure 13:
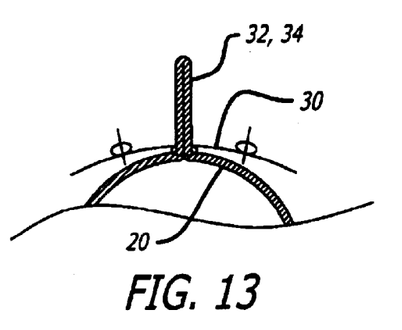
FIG. 13 is a cross-sectional view of a portion of a graft, depicting a plurality of folds constrained by sutures.
Figure 14:
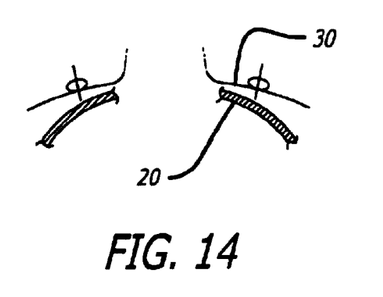
FIG. 14 is a cross-sectional view of a portion of the graft shown in FIG. 13, depicting an expanded configuration of the graft.

In a presently preferred embodiment, each of the sutures 30 are routed through one of the plurality of access holes 46, respectively. The access holes 46 can be identified by marking (not shown) the exterior of the jacket 40. Further, a legend can be provided to instruct an operator as to the function of a particular suture 30. For example, a first suture 50 can be identified as operating to affect the diameter of a superior end 52 of the graft 20. Each suture can have a different color that corresponds to the legend. The loop 62 of a particular suture 30 is secured by a knot 100 that is placed inside the jacket 40 (FIGS. 8–9). To release the pleat 34, the tail of the suture 30 is placed under tension to pull the knot 100 out through the access hole 46 of the jacket 40. Where necessary, the loop 62 may be cut and the suture 30 is pulled to accomplish providing the graft 20 with a particular size. Otherwise, when the knot 100 is in the form of a slip knot or chain stitch, pulling on the suture 30 will accomplish release of a pleat without the need for cutting.

With reference to FIGS. 11–14, it is further contemplated that the suture 30 can be passed through both sides of a fabric fold or pleat 32, 34 and re-routed back through the pleat 32, 34 again to thereby maintain the pleat. Varying the height of a pleat 32, 34 controls the amount of increase in dimension when the suture 30 is released. Although the figures depict longitudinal pleats, the same concept can be applied to lateral pleats.

Moreover, it is contemplated that a plurality of looped (or otherwise) sutures 30 (See FIGS. 12–14) of varying tensile strength can be employed to provide flexibility in modifying the profile of a graft 20 within vasculature. For example, by configuring a graft 20 with a pair of looped sutures 30 arranged 180° opposed and by applying a desired radial force, the suture 30 that embodies the lesser amount of tensile strength will break first. If it is found that the graft 20 fits as desired within the vasculature, no further radial force is applied. Otherwise additional radial force is applied to break the second looped suture 30. It is recognized that sutures having substantially identical tensile strength can be employed as such sutures can be manipulated to break as desired. It also is to be recognized that by configuring the outside of the graft 20 with pleats 32, 34, blood flow is presented with a relatively smooth inner surface. Moreover, the sutures 30 themselves remain out of the flow of blood.

The adjustable device can further include a crosspiece 60 that engages a loop 62 formed in a particular suture 30. It is contemplated that in one embodiment, the crosspiece 60 operates to retain the loop 62 in a position through an access hole 46 and exterior the jacket 40. To modify a particular dimension of the graft 20, the loop 62 is cut at the crosspiece 60 and the suture 30 is pulled to accomplish providing the graft 20 with a particular profile. The crosspiece 60 may be fabricated from any appropriate metal or plastic material.

Figure 5:
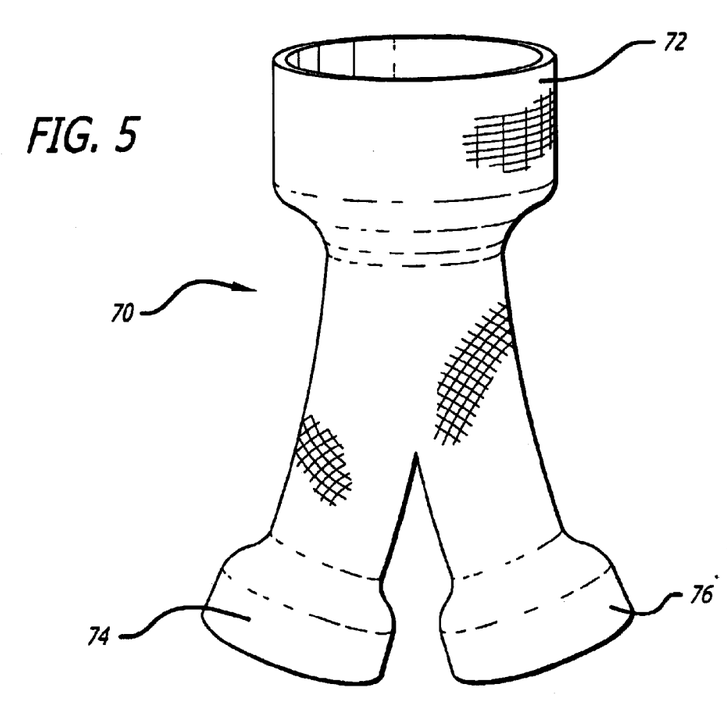
FIG. 5 is a perspective view, depicting an alternative embodiment of a graft of the present invention.
Figure 6:
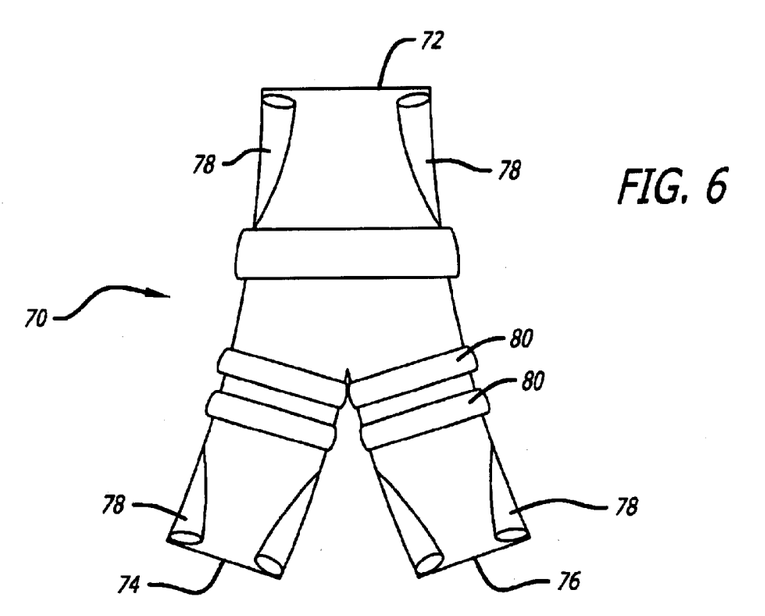
FIG. 6 is a perspective view, depicting the graft of FIG. 5 configured with a plurality of pleats.

In an alternative embodiment (FIGS. 5–7), a graft 70 of the present invention includes a flared superior end 72. Additionally, the terminal ends 74, 76 of the legs of the graft 70 may be similarly flared. It is contemplated that such a graft 70 can accommodate a greater range of main and branch diameters than a conventional non-flared graft. It also allows the pleat 78 to run a shorter distance in the axial or longitudinal direction, instead of requiring a full length pleat 78 for adjustment of a neck or limb diameter, for example.

Figure 7:
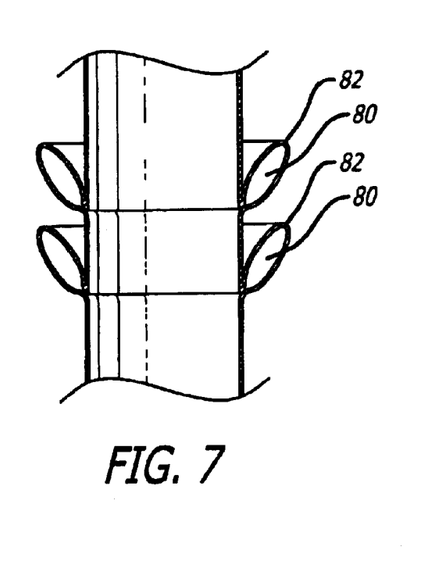
FIG. 7 is an enlarged cross-sectional view of a portion of the graft of FIG. 6.

As shown in FIG. 7, the transverse or longitudinal pleats 80 are folded to define a pocket 82. When the graft 70 is placed in vasculature, the pockets are intended to face away from the flow direction. Accordingly, although the pockets 80 are shown as being directed toward the superior end 72 of the adjustable graft 70, should the graft 70 be placed so that blood flows from the legs to the superior end 72 of the graft 70, the pockets 80 would be directed toward the legs of the graft 70. By so configuring the pockets 80, blood flow will not tend to open up the pocket 80 and blood flow is less likely to be disrupted.

Moreover, constructing the pleats 80 on the outside of the graft 20, 70 of the present invention, operates to preserve a smooth profile on the inside of the graft 20, 70 for optimal flow characteristics. Although seams are present on the inside of the graft 20, 70, these seams are tightly sewn to provide a continuous surface without ridges that may create a nidus for thrombus formation.

It is contemplated that the graft 20, 70 of the present invention is placed at a target site within a patient shortly after the performance of an aortogram or other procedure intended to map the target site. Upon so mapping the target site, one or more of the adjustment devices of the graft 20, 70 may be manipulated to accomplish configuring the graft as desired. Once the graft is fully configured, the remaining tails of the sutures 30 extending outside the jacket 40 are cut flush with the outer surface of the jacket 40. Where the jacket 40 is being used to facilitate delivery of the graft 20, 70 with a patient's body, reference is made to markers (not shown) on the jacket 40 to aid in selecting the proper adjustment devices. Where present and necessary, the crosspieces 60 are removed. Thereafter, using conventional methods, the assembly is advanced within the patient's body and to the target site, where the graft 20, 70 is implanted.

Thus, the graft 20, 70 of the present invention may be employed to treat a wide range of lumens having many variations of geometries. A significant advantage provided is that the graft 20, 70 can be customized to fit a target site contemporaneous to an implant procedure.

Additionally, the adjustable graft 20, 70 of the present invention can embody a modular design wherein various sections of a tube or bifurcated adjustable graft assembly can be mated in situ (for eg. See FIG. 15). Each of the modular sections 102 can themselves be pleated as necessary or where desired, certain of the modular sections can lack pleats. Additionally, adjustable grafts 20, 70 can be provided with access holes 104 through side walls for the purpose of accommodating blood flow in for example, the thoracic region of the aorta where branch vessels feed the brain or downstream in the aorta where branch vessel feed the kidneys. As such, the adjustable grafts can include "T" inlets or outlets.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A graft, comprising:
    a body, the body having a first length and a first lateral profile and configured to be delivered within vasculature by a catheter; and at least one adjustment device releasably attached to the body, the adjustment device defining structure separate from the body and the catheter;
    wherein manipulation of the adjustment device allows the body to assume a second length.

2. The graft of claim 1, wherein manipulation of the adjustment device allows the body to assume a second lateral profile.

3. The graft of claim 1, further comprising a plurality of adjustment devices releasably attached to the body, wherein manipulation of one of the plurality of adjustment devices allows the body to assume a second lateral profile.

4. The graft of claim 1, further comprising a plurality of adjustment devices releasably attached to the body, wherein manipulation of one of the plurality of adjustment devices allows the body to assume a third length.

5. The graft of claim 1, the graft further comprising at least one pleat.

6. The graft of claim 5, wherein the pleat extends longitudinally along the graft body.

7. The graft of claim 5, wherein the pleat extends laterally along the graft body.

8. The graft of claim 5, wherein the graft is adapted for placement within vasculature for blood flow, the pleat further comprising a fold defining a pocket, the pocket directed away from blood flow.

9. The graft of claim 1, the graft further comprising a plurality of pleats.

10. The graft of claim 9, wherein at least one of the plurality of pleats extends longitudinally.

11. The graft of claim 9, wherein at least one of the plurality of pleats extends laterally.

12. The graft of claim 1, wherein the graft body is bifurcated.

13. The graft of claim 1, wherein the graft has a first end and a second end, at least one of the first and second ends being layered.

14. The graft of claim 1, wherein the graft is adapted to be placed within a tubular jacket having at least one access hole.

15. The graft of claim 14, the tubular jacket further comprising a plurality of access holes.

16. The graft of claim 15, the tubular jacket further comprising identifiers marking each of the access holes.

17. A graft, comprising:
a body, the body having a first length and a first lateral profile; and
at least one adjustment device releasably attached to the body, the adjustment device defining structure separate from the body;
wherein manipulation of the adjustment device allows the body to assume a second length and the adjustment device further comprising a stitch loop.

18. The graft of claim 17, wherein a portion of the stitch loop is routed through the access hole.

19. The graft of claim 18, the adjustment device further comprising a crosspiece attached to a terminal end of the stitch loop.

20. A graft, comprising:
a body, the body having a first length and a first lateral profile; and
at least one adjustment device releasably attached to the body, the adjustment device defining structure separate from the body;
wherein manipulation of the adjustment device allows the body to assume a second length and said adjustment device further comprising a looped suture routed through a fold in the graft.

21. The graft of claim 20, said adjustment device further comprising a plurality of looped sutures routed through folds in the graft, at least one of said plurality of sutures having a tensile strength different from other of the plurality of sutures.

22. A graft, comprising:
a body, the body having a first length and a first width and configured to be delivered within vasculature by a catheter; and
at least one adjustable device releasably attached to the body and defining structure separate from the catheter;
wherein manipulation of the adjustment device allows the body to assume a second width.

23. The graft of claim 22, wherein manipulation of the adjustment device allows the body to assume a second length.

24. The graft of claim 22, further comprising a plurality of adjustment devices releasably attached to the body, wherein manipulation of one of the plurality of adjustment devices allows the body to assume a second length.

25. The graft of claim 22, further comprising a plurality of adjustment devices releasably attached to the body, wherein manipulation of one of the plurality of adjustment devices allows the body to assume a third width.

26. The graft of claim 22, the graft further comprising at least one pleat.

27. The graft of claim 26, wherein the pleat extends longitudinally along the graft body.

28. The graft of claim 26, wherein the pleat extends laterally along the graft body.

29. The graft of claim 26, wherein the graft is adapted for placement within vasculature for blood flow, the pleat further comprising a fold defining a pocket, the pocket directed away from blood flow.

30. The graft of claim 22, the graft further comprising a plurality of pleats.

31. The graft of claim 30, wherein at least one of the plurality of pleats extends longitudinally.

32. The graft of claim 30, wherein at least one of the plurality of pleats extends laterally.

33. The graft of claim 22, wherein the graft body is bifurcated.

34. The graft of claim 22, wherein the graft has a first end and a second end, at least one of the first and second ends being layered.

35. The graft of claim 22, wherein the graft is adapted to be placed within a tubular jacket having at least one access hole.

36. The graft of claim 35, the tubular jacket further comprising a plurality of access holes.

37. The graft of claim 36, the tubular jacket further comprising identifiers marking each of the access holes.

38. A graft, comprising:
a body, the body having a first length and a first width; and
at least one adjustable device releasably attached to the body;
wherein manipulation of the adjustment device allows the body to assume a second width and the adjustment device further comprising a stitch loop.

39. The graft of claim 38, wherein a portion of the stitch loop is routed through the access hole.

40. The graft of claim 39, the adjustment device further comprising a crosspiece attached to a terminal end of the stitch loop.

41. A graft, comprising:
a body the body having a first length and a first width; and
at least one adjustable device releasably attached to the body;
wherein manipulation of the adjustment device allows the body to assume a second width and said adjustment device further comprising a looped suture routed through a fold in the graft.

42. The graft of claim 41, said adjustment device further comprising a plurality of looped sutures routed through folds in the graft, at least one of said plurality of sutures having a tensile strength different from other of the plurality of sutures.

43. A method for preparing a graft for placement within vasculature by a catheter, the graft including a body and at least one adjustable device, the adjustable device defining structure separate from the body and the catheter, comprising the steps of:
performing an arteriogram prior to implant of the graft; and
manipulating the adjustment device independently of the catheter to customize the graft for placement within vasculature.

44. A method for preparing a graft for placement within vasculature by a catheter, the graft having a body and a plurality of adjustable devices attached thereto, the plurality of adjustable devices defining structure separate from the body and the catheter, comprising the steps of:

performing an arteriogram prior to implant of the graft;

applying a first force to the graft to activate a first adjustable device; and applying a second force to the graft to activate a second adjustable device.

* * * * *